United States Patent [19]

Long, Jr.

[11] Patent Number: 4,987,154

[45] Date of Patent: Jan. 22, 1991

[54] BIOCOMPATIBLE, STABLE AND CONCENTRATED FLUOROCARBON EMULSIONS FOR CONTRAST ENHANCEMENT AND OXYGEN TRANSPORT IN INTERNAL ANIMAL USE

[75] Inventor: David M. Long, Jr., El Cajon, Calif.

[73] Assignee: Alliance Pharmaceutical Corp., San Diego, Calif.

[21] Appl. No.: 82,846

[22] Filed: Aug. 5, 1987

Related U.S. Application Data

[63] Continuation-in-part of Ser. No. 818,690, Jan. 14, 1986, Pat. No. 4,865,836.

[51] Int. Cl.$^5$ .............................................. A61K 47/00
[52] U.S. Cl. .................................. 514/772; 514/788; 514/832; 424/5
[58] Field of Search .................... 424/5; 514/832, 833, 514/772, 788

[56] References Cited

U.S. PATENT DOCUMENTS

| | | | |
|---|---|---|---|
| 3,818,229 | 6/1974 | Long, Jr. | 250/312 |
| 3,962,439 | 6/1976 | Yokoyama et al. | 514/832 |
| 3,975,512 | 8/1976 | Long | 424/5 |
| 4,073,879 | 2/1978 | Long, Jr. | 424/5 |
| 4,105,798 | 8/1978 | Moore et al. | 514/435 |
| 4,146,499 | 3/1979 | Rosano | 252/186 |
| 4,343,797 | 8/1982 | Ecanow | 514/832 |
| 4,397,870 | 8/1983 | Sloviter | 424/325 |
| 4,423,077 | 12/1983 | Sloviter | 514/832 |
| 4,439,424 | 3/1984 | Ecanow | 514/832 |
| 4,451,251 | 5/1984 | Osterholm | 604/24 |
| 4,497,829 | 2/1985 | Sloviter | 514/832 |
| 4,605,786 | 8/1986 | Yokoyama et al. | 514/832 |
| 4,613,708 | 9/1986 | Riess et al. | 514/832 |
| 4,640,833 | 2/1987 | Tamborski et al. | 514/832 |
| 4,654,337 | 3/1987 | Yokoyama et al. | 514/832 |
| 4,895,876 | 1/1990 | Schweighardt et al. | 514/747 |

FOREIGN PATENT DOCUMENTS

| | | | |
|---|---|---|---|
| 0220153 | 10/1986 | European Pat. Off. | |
| 023109 | 1/1987 | European Pat. Off. | |
| 0231070 | 8/1987 | European Pat. Off. | |
| 2105287 | 4/1972 | France | |
| J58032 | 8/1981 | Japan | |
| J59046 | 9/1982 | Japan | |
| J59067 | 10/1982 | Japan | |
| 58-96061 | 6/1983 | Japan | 424/5 |
| J60166 | 2/1984 | Japan | |
| 59-67229 | 4/1984 | Japan | 424/5 |

OTHER PUBLICATIONS

Reiss, Jean G.; Artificial Organs 8:34–56 (1984).
Geyer, R., "Perfluorocarbon Blood Substitutes", Intl. Symp. on Artificial Blood Substitutes, Bari, Italy: Jun. 19–20, (1987), pp. 45–67.
Persico, D. et al., J. Org. Chem. 50:5156–5159 (1985).
Sharts, C. and H. Reese, The Solubility of Oxygen in Aqueous Fluorocarbon Emulsions, J. Fluorine Chemistry 11:637–641 (1978).
Riess, J., International Symposium on Blood Substitutes, Bari, Italy: Jun. 19–20, 1987, Proceedings pp. 135–166.
Davis, S.; Advances in Clinical Nutrition, 19:213–239 (1982).
Yokoyama, K. et al., Fed. Proc. 34(6) 1478–1483 (1975).
Steiner, M. and J. Anastasi, Vitamin E: An Inhibitor of the Platelet Release Function, J. Clinical Invest. 57:732–737 (1976).
Pandolfe, W. D. and R. R. Kinney, National Meeting of the American Institute of Chemical Engineers, Denver, Colo., Aug. 29, 1983.
Gould, S. et al., The Journal of Trauma 23(8): 720–724 (1983).
Moss, G. Polyhemoglobin and Fluorocarbon as Blood Substitutes, Biomaterials, Artificial Cells, and Artificial Organs 15(2): 333–336 (1987).
Geyer, R., "Perfluorocarbons as Oxygen Transport Vehicles", Biomaterials Artificial Cell (as above) 15(2): 329–333 (1987).
Burgan, A., D. M. Long et al. (as above) 15(2): 403(1987).
Police, A. M. et al., Critical Care Medicine 13(2): 96–98 (1985).
Nunn, G. R. et al., American J. of Cardiology 52: 203–205 (1983).

(List continued on next page.)

*Primary Examiner*—Frederick E. Waddell
*Attorney, Agent, or Firm*—Knobbe, Martens, Olson & Bear

[57] ABSTRACT

An up to 125% fluorocarbon emulsion for use in or with animal bodies and organs thereof, maintains emulsion stability through normal sterilization procedures with selective osmotic and buffering agents, maintains the emulsion at within predetermined osmolarity levels and, when desired, free of excessive calcium precipitation, reduces in vivo and in vitro red blood cell injury, reduces adverse anemia effects, reduces viscosity and reduces the rate of oxidation, and tends to equilibrate its distribution in major body organs thereby reducing toxicity. The osmotic agents may buffer and may provide nutrient in the form of sugars. The osmotic and buffering agents can comprise, selectively, hexahydric alcohols, namely mannitol and sorbitol; certain sugars, namely glucose, mannose and fructose; along with buffering agents that will affect osmolarity including imidazole, tris(hydroxymethyl)aminomethane, sodium chloride, sodium bicarbonate, monobasic potassium phosphate, dibasic potassium phosphate, calcium chloride, magnesium sulfate, monobasic sodium phosphate, dibasic sodium phosphate or combinations of them. The emulsion may include tocopherol. A method of emulsifying the fluorocarbon includes forced flow impingement under pressure after mixing the fluorocarbon into the discontinuous phase. The fluorocarbon emulsion can be used to deliver drugs and medicines soluble in, or transportable by the emulsion.

47 Claims, No Drawings

OTHER PUBLICATIONS

Patel, M. et al., Federation Proceedings 29(5): 1740–1745 (1970).
Bose, B. et al., Brain Research 328: 223–231 (1985).
Spears, J. et al., Myocardial Protection with Fluosol-DA During Prolonged Coronary Balloon Occlusion in the Dog, 68 (Supp. III) No. 317, Oct., 1983.
Peck, W. W. et al., Investigative Radiology 19:129 (1984).
Dobben, G. et al., Neuroradiology 6: 17–19 (1973).
Brahme, F. et al., Acta Radiologica, Supplement 347: 459–466 (1975).
Liu, M. S. et al., Myleography with Perfluoroctylbromide: Comparison with Patopaque, Investigative Radiology 11(4): 319–330 91976).
Long, D. M. et al., Efficacy and Toxicity Studies with Radiopaque Perfluorocarbon, Radiology 105(2): 323–332 (1972).
Itoh, Y. et al., Gan To Kagaku Ryoho 1(4): 864–872 (1984).
Rockwell, S., "Perfluorochemical Emulsions as Adjuncts to Radiotherapy", 3rd Biomaterials, etc. 15(2): 430(1987).
Burgan, A. et al., "Acute and Subacute Toxicity of 100% PFOB Emulsion", 5th Annual Mtng. Soc. of Magnetic Resonance in Med. Montreal: Aug. 18–22, 1986.
Long, D. et al., Total Exchange Perfusion, International Symposium Centenary of the Discovery of Fluorine, Paris, Aug. 25–29, 1986.
Long, D. C. et al., Biomaterials, etc. 15(2): 417(1987).
Long, D. M. et al., "Experimental and Clinical Applications of PFOB", same as above 15(2): 418(1987).
Arlen, C., Long, D. et al., same as above 15(2): 431(1987).
"Patent Abstracts of Japan", vol. 10, No. 13 (C-323), [2070], Jan. 18, 1986, p. 44C323 and JP-A-60 166 626 (Midori Juji K.K.), Aug. 29, 1985.

BIOCOMPATIBLE, STABLE AND CONCENTRATED FLUOROCARBON EMULSIONS FOR CONTRAST ENHANCEMENT AND OXYGEN TRANSPORT IN INTERNAL ANIMAL USE

RELATION WITH RELATED APPLICATION

This application is a continuation-in-part application of application Ser. No. 818,690, now U.S. Pat. No. 4,865,836, filed Jan. 14, 1986 in the name of David M. Long, Jr. and entitled, "Brominated Perfluorocarbon Emulsions for Internal Animal Use for Contrast Enhancement and Oxygen Transport." Priority of subject matter in this application common with subject matter in that patent is hereby claimed.

BACKGROUND OF THE INVENTION

1. Field of the Invention

The present invention relates to the art of non-toxic oxygen transport and contrast enhancement agents for internal and external animal use, and more particularly to stable high concentration fluorocarbon emulsions capable of sterilization and which are selectively free of calcium precipitation, reduce in vivo and in vitro red blood cell, or erythrocyte, injury, reduce anemia effects, and have reduced viscosity and reduced rate of oxidation or free radical damage, particularly of components of the emulsion and of contacted body tissue.

2. Description of the Prior Art

In the past, efforts to use emulsified fluorocarbons as an oxygen transport or carrier, as in a blood substitute, and as a contrast enhancement agent, as for X-ray, ultrasound and magnetic resonance imaging, have encountered certain difficulties. Purity, non-toxicity, chemical and biological inertness and ability to excrete are desirable objectives. The emulsified fluorocarbon must be capable of sterilization, preferably by heat, have long-term size and function stability preferably in the fluid state, be industrially feasible, persist for sufficiently long or effective times in the blood stream when used intravascularly and be eliminated sufficiently rapidly from the body.

For intravenous use, it is considered important to have small particle size. However, long term storage for extended periods of time for a month or longer, of blood substitutes has heretofore resulted in conglomeration or coalescence of the fluorocarbon particles in the emulsion into larger particles, especially after heat sterilization. For a general discussion of the objectives and a review of the efforts and problems in achieving these objectives in fluorocarbon blood substitutes, see "Reassessment of Criteria for the Selection of Perfluoro Chemicals for Second-Generation Blood Substitutes: Analysis of Structure/Property Relationship" by Jean G. Riess, 8 *Artificial Organs*, 34–56, (1984).

Larger particle sizes are dangerous in intravenous use in that they tend to collect in the lung, liver, spleen and some other organs, enlarging them and endangering their functioning. On the other hand, it is desired to have sufficient particle size in the fluorocarbon particles for them to collect in tumors and other areas when fluorocarbons are used as a contrast enhancement medium. Larger particle sizes within reasonable limits, also, are unobjectionable when used in other, non-venous systems in the body, such as, for example, the cerebrospinal fluid ventricles and cavities.

In the past, it has been observed that fluorocarbon emulsions used intravascularly accumulate disproportionately more in the spleen, as opposed to other organs such as the liver. This concentration in the spleen sometimes causes a transient hypersplenism, a condition characterized by an enlarged and over-active spleen from which a transient anemia results. A fluorocarbon emulsion having the above-indicated characteristics but also having a more even distribution among the major body organs is desired.

Glycerol is normally a good osmotic agent for fluorocarbon emulsions, but in concentrations has been observed to hemolize the red blood cells. The glycerol apparently swells the red blood cells, damaging the cells, promoting the egress of hemoglobin and thus causing damage to the cells. Certain other additives, notably sugars have similar red blood cell damaging effects. It has long been desired to avoid or to limit the amount of such hemolytic agents in the emulsion.

It is known that lecithin and other phospholipids are subject to oxidation in the vascular system. Such oxidation of lecithin phospholipids is also observable in respect to the lecithin phospholipid emulsifier components of stored or packaged fluorocarbon emulsions. It is desired to have effective, stable and non-toxic fluorocarbon emulsions having phospholipid emulsifying agents or other oxidizable components wherein oxidation is inhibited.

It is frequently desired to have high concentration fluorocarbon emulsions, but they unfortunately tend to have high viscosity. It may also be desired to have emulsions containing nutrients, such as glucose and like sugars. Glucose, however, has been known to make fluorocarbon emulsions more viscous. It is desired to have fluorocarbon emulsions that are less viscous and more fluidic, to facilitate packaging, injectability and avoidance of blood vessel blockage.

It has been desired, further, to provide a vehicle carrier for delivering fat or oil soluble and fluorocarbon soluble medicines through the intravascular, intraperitoneal, oral, respiratory, cerebrospinal and other internal animal body tissue or systems, including human tissue, as well as for delivering such medicines externally such as cutaneously through the skin. "Tissue" in this specification will be used to include blood.

It is often desirable to have some emulsions which contain or deliver calcium, and which do not have calcium precipitating components. Many buffers, however, are phosphates or carbonates and form excessive calcium precipitates which not only reduce the amount of calcium available for therapeutic use, but dangerously deposit calcium compounds in the tissue.

The present invention is directed toward improvements in the formulation and use of fluorocarbon emulsions to meet these and other objectives while providing a stable, non-toxic and efficacious fluorocarbon emulsion.

SUMMARY

In brief, in accordance with one aspect of the invention, fluorocarbon emulsions having a concentration in the continuous phase of from 20% to 125% weight per volume is described whose mean particle size and particle distribution is maintained substantially stable through normal sterilization and storage procedures. Hereinafter in this specification, all definitions and references given in the co-pending application Ser. No. 818,690, now U.S. Pat. Ser. No. 4,865,836 are incorporated herein as though fully set forth as and for definitions and references in this application. The continuous phase of the emulsion shall be used herein to refer to the aqueous phase of the emulsion. In particular, for example, the term "weight per volume" or "w/v" will be used and should be understood to mean the ratio of the weight in grams per 100 cubic centimeters or 100 milliliters, or equivalent expressions or mathematical identities thereof.

The fluorocarbon in emulsion may be monobrominated perfluorocarbons, such as 1-bromoseptadecafluoroctane (C8F17Br, sometimes designated perfluoroctylbromide or "PFOB"), 1-bromopentadecafluoroseptane (C7F15Br), and 1-bromotridecafluorohexane (C6F13Br), sometimes known as perfluorohexylbromide or "PFHB"), C4F9CH-CHC4F9 ("F-44E"), i-C3F7CH-CHC6F13 ("F-i36E"), C6F13CH=CHC6F13 ("F-66E"), F-adamantane ("FA"), F-1,3-dimethyladamantane ("FDMA"), F-declin ("FDC"), F-4-methyloctahydroquinolidizine ("FMOQ"), F-4-methyldecahydroquinoline ("FHQ"), F-4-cyclohexylpyrrolidine ("FCHP"), F-2-butyltetrahydrofuran ("FC-75"), (CF3)2CFO(CF2CF2)2OCF(CF3)2, (CF3)2CFO(CF2CF2)3OCF(CF3)2, (CF3)2CFO(CF2CF2)2F, (CF3)2CFO(CF2CF2)3F, (C6F13)2O and F[CF(CF3)CF2O]2CHFCF3.

The emulsion has for an emulsifying agent a phospholipid, an anionic surfactant, a fluorosurfactant or combinations thereof.

Osmolarity is maintained by an osmotic agent which has benefit independent of osmolarity, such as the hexahydric alcohols, namely mannitol and sorbitol which also are used to control viscosity and stabilize particle membrane structure. Other osmotic agents, such as certain sugars, namely glucose, mannose and fructose may be used which provide nutrition. Osmolarity is also affected by buffers, which are selected from imidazole or tris(hydroxymethyl)aminomethane, which do not precipitate calcium, or may be selected from such buffering agents as sodium chloride, sodium bicarbonate, magnesium chloride, monobasic potassium phosphate, dibasic potassium phosphate, calcium chloride, magnesium sulfate, monobasic sodium phosphate and dibasic sodium phosphate. Certain biocompatible combinations of these osmotic agents provide variously or inclusively for reduction of red blood cell injury in vivo and in vitro, for reduction of viscosity, for reduction in the rate of oxidation, for nutrition and for buffering the acidity or pH level. Tocopherol, mannitol, ascorbyl palmitate and imidazole may be added or increased to further reduce the rate of oxidation of the emulsion components in vitro, and also are believed to have similar effects in vivo to reduce the rate of oxidation of the body tissue or organ to which the emulsion may be applied.

A buffering agent maintains the pH at predetermined levels, and may provide osmotic pressure to maintain osmolarity. The buffering agents may include the non-calcium precipitating buffers imidazole, tris(hydroxymethyl)aminomethane and other buffering agents such as sodium bicarbonate, monobasic potassium phosphate, dibasic potassium phosphate, monobasic sodium phosphate and dibasic sodium phosphate. Tris(hydroxymethyl)aminomethane is sometimes called THAM, or by several of its trade names, such as, for example, Trizma by Sigma Chemical Company of St. Louis, Missouri.

The fluorocarbon emulsions are prepared, as set forth in my co-pending application Ser. No. 818,690, now U.S. Pat. No. 4,865,836, first by mixing in the aqueous or continuous phase the "vehicle" by adding osmotic agent(s), buffering agent(s), electrolytes if desired, emulsifying agent(s) and additional anti-oxidant(s) if desired. The fluorocarbon is mixed into the vehicle at a tempered rate so that the emulsion is tempered or homogeneous. The emulsion is then divided into separate flows which are impinged at high velocities upon each other in sheets in a cavity under relatively high pressure. The emulsions are then filtered, packaged, sterilized and otherwise processed for storage and use.

Other novel features which are believed to be characteristic of the invention, both as to organization and methods of operation, together with further objects and advantages thereof, will be better understood from the following description in which preferred embodiments of the invention are described by way of example.

DESCRIPTION OF THE PREFERRED EMBODIMENTS

A fluorocarbon emulsion comprises a continuous, i.e. aqueous phase and a discontinuous phase. The discontinuous phase comprises the fluorocarbon with an emulsifying agent. Osmotic agents and biological pH buffers are included generally in the continuous phase to maintain osmolarity and pH.

The emulsifying agent generally surrounds and forms a layer around the discontinuous phase creating essentially fluorocarbon particles suspended within the continuous phase. Lecithin is used frequently as the emulsifying agent, as better described in my co-pending application referenced hereinabove. Other emulsifying agents may be used with good effect, such as fluorinated surfactants, also known as fluorosurfactants and anionic surfactants. Fluorosurfactants which will provide stable emulsions include triperfluoroalkylcholate [C7F15C(=O)O]3, perfluoroalkylcholestanol [C7F15C(=O)O], perfluoroalkyloxymethylcholate, XMO-10 and fluorinated polyhydroxylated surfactants, such as, for examples, those discussed in "Design, Synthesis and Evaluation of Fluorocarbons and Surfactants for In Vivo Applications New Perfluoroalkylated Polyhydroxylated Surfactants" by J. G. Riess, et al. Such fluorosurfactants discussed therein include a fluorophilic tail, a hydrocarbon prolongator, a junction unit comprised of an ether, an ester or an amide, and a hydrophilic head. Fluorophilic tails include, for example, C3(CF2)n, where n equals from 4 to 10. XMO-10 is a fluorinated surfactant having a formula C3F7O(CF2)3C(=O)NH(CH2)3N(=O)(CH3)2. To be an non-toxic fluorosurfactant, the fluorinated surfactant and the fluorocarbon should have an elimination rate from the animal body or organ such that the fluorocarbon and the fluorinated cosurfactant are eliminated from the body or organ before carcinosis, teratogenesis or embryotoxicity occurs. Suitable anionic surfactant which will provide a stable, non-toxic and biocompatible emulsion are polyoxyethylene-polyoxypropylene copolymers.

The osmolarity of normal, for example human tissue is approximately from 290 milliosmols to 300 milliosmols. Maintaining this osmolarity is important in preventing injury to cells, such as red blood cells and endothelial cells which line the blood vessels into which, for example, the emulsion may be injected. When the osmolarity is less than 290 milliosmols, down to 200 milliosmols, water tends to diffuse into the cells causing them to swell and sometimes burst. When the osmolarity is too high, on the order of greater than 700 milliosmols, the cells lose water and may shrink. Injection of hyperosmotic medicines often are painful and burn, and further may also cause clotting and obstruction of the veins. These complications may be prevented by controlling the osmolarity of the emulsion prior to administration.

Fluorocarbon emulsions with low osmolarity tend to show instability in coalescense of the discontinuous particles, especially when subjected to stress shelf life studies such as freeze and thaw cycles. Normally when the osmolarity is too high, on the order of greater than 650 milliosmols, the fluorocarbon emulsion particles tend to aggregate, which can lead to coalescence and separation of the emulsion. It has been found, however, that in formulating fluorocarbon emulsions, slight hyperosmolarity, in the range of from 300 milliosmols to approximately 450 milliosmols is favored in order (1) to protect more against freezing and thus to obtain more stability, and (2) to accommodate increased amounts of the osmotic and other active agents, especially where the osmotic agent has therapeutic and other beneficial effects, as will be explained more below.

In the preferred embodiment of the present invention, mannitol is added to the emulsion. It has been found that mannitol provides a means for maintaining osmolarity, for reducing red blood cell injury, for reducing viscosity, for providing anti-oxidant effects in the emulsion and for stabilizing the fluorocarbon particles. Because mannitol has such beneficial effects, greater amounts of mannitol can be tolerated in the body's tissues. When using mannitol as the osmotic agent, for example, the stability of the emulsion can be maintained at the desired osmolarity range of from 240 milliosmols to 650 milliosmols with from 0.25% weight per volume to 1.5% weight per volume. The body's tissues can tolerate substantially more mannitol for obtaining anti-oxidation effects, for emulsion stabilizing effects, for viscosity reducing effects and for red blood cell protection effects.

It is believed, further, that mannitol is responsible for an observed improvement in the distribution of the fluorocarbon emulsion particles among the major organs when applied within the animal body. The effects of mannitol are believed to reduce organ toxicity, which in turn is believed to largely account for the reduction of adverse anemia effects when using the emulsion.

It is believed that mannitol is incorporated into or interacts in some way with the lecithin or other emulsifier membrane of the fluorocarbon particle in emulsion, to form a more protective membrane. For lecithin, this interaction is believed to be a more competent cell barrier structure that is more renitent in the membrane. It is believed, further, that the mannitol does not adversely affect the stability of the particle size in the fluorocarbon emulsion, as will be discussed in greater detail below.

Additionally, the mannitol, it is believed, assists in forming a more competent and renitent cell barrier in the somewhat similar lecithin membrane barriers of red blood cells, thus protecting against injury to the red blood cell, which injury allows hemoglobin to escape. Reduction of red blood cell injury has been observed with mannitol added to the emulsion in both in vivo and in vitro experiments.

Glycerol has been used as an osmotic agent, but glycerol readily penetrates the red blood cell walls. This penetration causes swelling of the red blood cells allowing their hemoglobin to escape. The escape of hemoglobin results in red blood cell ghosts which cannot transport oxygen. This condition may contribute to observed transient anemia effects with high doses of fluorocarbon emulsions. Mannitol is preferred as the osmotic agent to glycerol where injury to red blood cells may be a problem.

Mannitol establishes an osmotic pressure in the continuous phase of the emulsion, and is preferred in the present invention as an osmotic agent. Mannitol, unlike other osmotic agents, such as, for examples, glucose, glycerol and saline, generally does not penetrate the red blood cell, and generally does not cause the red blood cells to swell and be damaged. Swollen and damaged red blood cells allow hemoglobin to be released from the red blood cell, thus possibly contributing to the observed anemia effects.

The use of mannitol in the fluorocarbon emulsion, it is believed, reduces the temporary anemia effects sometimes observed during discrete time periods in animals after receiving exaggerated doses of perfluorocarbon emulsion. It is believed that the highly desired and long sought reduction in anemia effects is due to distribution equilibration of the fluorocarbon emulsion among the body organs by mannitol, and to reduction of red blood cell injury. This reduction in anemia effects has been observed in adolescent Sprague Dawley rats, as may be better seen in the following Examples I and II.

EXAMPLE I

Two grams per kilogram of body weight of a 100% weight per volume emulsion of perfluoroctylbromide were infused intravenously into twenty-two Sprague Dawley rats, some (ten) of the rats getting an emulsion having 0.6% weight per volume of mannitol while other rats (twelve) received an emulsion having no mannitol but having a saline concentration providing equivalent osmotic pressure. There were ten other control rats which received a placebo injection of physiologic saline in a dose of two milliliters per kilogram of body weight. The emulsion was further comprised of 6% weight per volume of lecithin, 0.0252% weight per volume of THAM. The emulsion was prepared in accordance with the process and procedure given in my co-pending application referenced hereinabove. At two weeks, the rats receiving the emulsion including mannitol had in their red blood cells an average of 97% of hemoglobin (measured in grams/deciliter) as found in the control rats. The rats receiving the emulsion having no mannitol had at two weeks an average of 91% blood hemoglobin as compared to the control rats. The hemoglobin was measured by hemolyzing the red blood cells in the blood and measuring the amount of hemoglobin released.

EXAMPLE II

Rats of the same type as used in Example I were used in further tests, into which rats ten grams per kilogram of body weight of the emulsions as described for Example I above, were injected intravenously. At two weeks, the rats receiving the emulsion containing mannitol averaged 87% hemoglobin as compared with the control rats. The rats receiving the emulsion not having the mannitol averaged 70% hemoglobin at two weeks.

Mannitol thus was successful in reducing anemia effects even in rats receiving very high doses of fluorocarbon emulsions.

More significantly affecting these reductions in anemia effects, it is believed, is the observed difference in major body organ distribution resulting from using mannitol as an osmotic agent and as an emulsion stabilizer over other osmotic agents. As noted, it has been observed in the past that fluorocarbon emulsions accumulate more in the spleen, on the order of 10 to 15 times more than in other organs such as the liver. It is believed that this high concentration of fluorocarbon emulsion particles in the spleen is caused by the macrophages engulfing the particles and trapping them in the spleen. This large accumulation is unnecessary for effective imaging and sometimes causes hypersplenism, a condition characterized by an enlarged and over-active spleen from which anemia may result. When using mannitol as the osmotic agent, this accumulation is significantly reduced, on the order of approximately forty-eight percent (48%) as may be appreciated from the following Example III. Thus, the risk of hypersplenism and accompanying anemia is believed to be significantly reduced. This more equilibrated distribution can be seen better from the following experiment given by way of example:

EXAMPLE III

A dose of the 100% weight per volume perfluoroctylbromide emulsion having 0.6% weight per volume of mannitol comprising one gram per kilogram of body weight was injected intravenously into adolescent Sprague Dawley rats, and the level of concentration of the perfluoroctylbromide in the spleen was measured at twenty-four hours. The concentration was measured at $30.1 \pm 1.5$ milligrams per gram of spleen tissue. A substantially comparable 100% emulsion not having mannitol has typically in the past resulted in, for example, $57.61 \pm 2.345$ milligrams per gram of spleen tissue for the same dose.

Other organs, such as the liver showed a slight increase in perfluoroctylbromide concentration when using the same mannitol containing emulsion. In the rats receiving the emulsion with mannitol, a concentration of $5.6 \pm 0.14$ mg/gm. liver tissue was observed, as compared with $4.605 \pm 0.533$ mg./gm. liver tissue in a typical 100% emulsion not containing mannitol.

The anemia is very significantly and substantially reduced if not virtually eliminated altogether when mannitol is incorporated into the fluorocarbon emulsion.

Mannitol is, further, an anti-oxidant interacting with the free radicals in the body's systems generally, as well as with free radicals in stored emulsion. Further, it has been found that mannitol reduces the viscosity of the emulsion. With mannitol, reduced viscosity is observed in high concentration fluorocarbon emulsions and in fluorocarbon emulsions in which glucose or other nutrients have been added. As noted, glucose has been found to make fluorocarbon emulsions more viscous, but it has been observed that adding mannitol to such an emulsion restores viscosity to even less than the viscosity of an emulsion without glucose.

The anti-oxidation characteristics of the emulsion are improved dramatically by adding tocopherols, such as alpha tocopherol acetate, as may be seen from the results of experiments given in the following Example IV.

EXAMPLE IV

Fluorocarbon emulsions were prepared without mannitol or tocopherol (Batch I in the table 1 below), with mannitol but without tocopherol (Batch II in the table 1 below), with tocopherol but without mannitol (Batch III in the table 1 below) and with mannitol and tocopherol together (Batch IV in the table 1 below). In Batch II, mannitol was added in the amount of 0.6% weight per volume in the emulsion. Batch III had 0.05% weight per volume in alpha tocopherol acetate added. Batch IV comprised 0.6% weight per volume of mannitol and 0.05% weight per volume of alpha tocopherol acetate. The emulsions were 100% weight per volume perfluoroctylbromide emulsions having as the emulsifying agent 4.5% weight per volume lecithin, and further having 0.0252% weight per volume of THAM as a buffer to maintain the pH before the experiment and storage at 7.6, having 0.2% weight per volume of glucose for osmolarity, having 0.025% weight per volume of calcium chloride (CaCl), having 0.005% weight per volume of magnesium sulfate (MgSO4), and having water (H$_2$O) quantity sufficient to form the remainder of the emulsion.

All emulsions were saturated with oxygen at the time of preparation. Oxygenation was accomplished by sparging with 100% oxygen during the formulation of the emulsion. Additionally, twenty milliliters (ml) of the emulsion were placed in a 30 ml bottle having the head space filled with 100% oxygen. The bottle was sealed.

Thereafter, the oxygenated emulsions were then sterilized at 121 degrees Centigrade for eight minutes by autoclaving. Measurements of the partial pressure of oxygen (pO2), partial pressure of carbon dioxide (pCO2), and hydrogen ion concentration (pH) were taken at ten days and thirty days, where the atmospheric pressure varied during the measurements from 741 mm of mercury (Hg) to 746 mm Hg. Measurements were taken at 38 degrees Centigrade. The results are given in table 1 below, where in the first column are given the partial pressures of oxygen (pO2), in the second column are given the partial pressures of carbon dioxide (pCO2) and in the third column are given the resultant pH. The tocopherol used was alpha tocopherol acetate in a concentration of 0.05 grams per 100 milliliters of emulsion. The mannitol was 0.6 grams per milliliter of emulsion. Readings were taken at ten (10) days and thirty (30) days after preparation of the emulsion, and the emulsion was stored at 10 degrees Centigrade. All measurements except for pH are given in millimeters of Hg.

TABLE 1

| Batch | 10 days | | | 30 days | | |
|---|---|---|---|---|---|---|
| | pO2 | pCO2 | pH | pO2 | pCO2 | pH |
| I | 550.0 | 10.2 | 3.3 | 242.4 | 12.8 | 3.2 |
| II | 650.1 | 0.7 | 7.171 | 643.4 | 1.2 | 7.072 |
| III | 627.3 | 0.5 | 7.361 | 656.4 | 1.4 | 7.098 |
| IV | 738.3 | 0.25 | 7.436 | 664.6 | 0.94 | 7.191 |

Since the emulsion was saturated with water, approximately 47 mm Hg of the total 741 to 746 mm Hg pressure should be attributed to H$_2$O vapor. The emulsion having no mannitol, tocopherol or any other effective anti-oxidant shows a significant reduction in oxygen content occurring, and an increase in CO2 content with a pronounced acidity. No such deleterious effect occurs with the addition of mannitol, tocopherol or both. It can be observed that with mannitol and tocopherol used together, the emulsion becomes super-saturated with oxygen at ten days. At other times, the saturation of oxygen remains very high, close to full saturation at ten and at thirty days for emulsions with mannitol and/or tocopherol added, with time having some effect.

As noted hereinabove, mannitol does not decrease the stability of the particle sizes in the emulsion. It is believed that mannitol actually improves the particle size stability by forming a protective interaction with the lecithin membrane to protect the fluorocarbon particles and prevent the particles from coalescing.

It has also been found that glucose is an effective osmotic agent and works well in fluorocarbon emulsions. The particle size characteristics of the emulsion are not degraded with glucose being used as an osmotic agent, it has also been found. Other sugars, such as mannose and fructose are effective osmotic agents, and are also metabolized in cells of the body to provide sources of energy. It is often desired, further, to have glucose in the emulsion as a nutrient.

It is believed that glucose, like mannitol, interacts with, or is incorporated in the lecithin membrane of the fluorocarbon particle to protect or stabilize the fluorocarbon particle membrane. This protection is particularly effective in freeze - thaw cycle accelerated shelf life studies. In such studies, it has been found that the particle size means remained substantially the same through as many as five rapid freezes to minus 20 degrees Centigrade, each followed by thawing at room temperatures.

The most common buffering agents normally include phosphate compounds. It is frequently desired, however, to include calcium containing compounds in the emulsion as an additional electrolyte and as a nutrient, in particular when perfusing the heart and the cerebroventricular systems. Calcium is essential, for example, for the heart muscle to contract. Calcium containing compounds, however, such as calcium chloride (CaCl) will form calcium precipitates with phosphate and carbonate buffers. Excessive amounts of such precipitates are harmful in the vascular and some other body systems, in that calcium precipitates block vessels. In this specification, the term "non-calcium precipitating" will be used to designate a mixture or solution which has substantially no calcium precipitates or has calcium precipitates in such small quantity so as not to result in undesired or harmful body reactions.

The hydrogen ion concentration (pH) of fluorocarbon emulsions is related to the emulsion stability and biological tolerance. Acidic pH reduces the electronegativity of the particles, which encourages aggregation and sedimentation. Alkaline pH tends to stabilize the emulsion by increasing electronegativity. Alkaline emulsions with a pH of up to 8.2 are well tolerated when injected into the coronary arteries. When the pH is less than 7.0, the emulsion may cause decreased contractility of the heart muscle and ventricular fibrillation. For intracoronary use, the pH should be from 7.0 to 7.8. An emulsion with a pH of between 4.0 and 8.4 can be used intravenously and in certain other arteries such as the femoral artery depending upon the purpose of the use.

Tris(hydroxymethyl)aminomethane, sometimes called THAM, is an effective buffering agent for fluorocarbon emulsions to maintain the pH at predetermined levels. THAM, also, is non-calcium precipitating; that is to say, THAM does not precipitate calcium salts.

It has also been found that imidazole is a very effective buffering agent for use in fluorocarbon emulsions. Imidazole is, also, non-calcium precipitating.

Both THAM and imidazole have an effect on the osmolarity of the emulsion. Use of imidazole or THAM increases the alkalinity of the emulsion, and normally would be used in conjunction with other osmotic agents to maintain the osmolarity without causing the pH to vary beyond desired levels.

If calcium is not desired or if moderate amounts of calcium precipitates can be tolerated, phosphate and carbonate buffers, including monobasic sodium phosphate, dibasic sodium phosphate, monobasic potassium phosphate, dibasic potassium phosphate, sodium bicarbonate and combinations including these buffers will be suitable.

The osmotic agents and buffers discussed herein are effective for formulating several stable, non-toxic and/or efficacious fluorocarbon emulsions. For a stable emulsion, the fluorocarbon in emulsion may be monobrominated perfluorocarbons, such as 1-bromoseptadecafluoroctane ($C_8F_{17}Br$, sometimes designated perfluoroctylbromide or "PFOB"), 1-bromopentadecafluoroseptane ($C_7F_{15}Br$), and 1-bromotridecafluorohexane ($C_6F_{13}Br$, sometimes known as perfluorohexylbromide or "PFHB"). Other stable fluorocarbon emulsions are $C_4F_9CH\text{-}CHC_4F_9$ (sometimes designated "F-44E"), $i\text{-}C_3F_7CH\text{-}CHC_6F_{13}$ ("F-i36E"), and $C_6F_{13}CH{=}CHC_6F_{13}$ ("F-66E"), $C_{10}F_{18}$ ("F-declin"), F-adamantane ("FA"), F-methyladamantane ("FMA"), F-1,3-dimethyladamantane ("FDMA"), F-declin ("FDC"), F-4-methyloctahydroquinolidizine ("FMOQ"), F-4-methyldecahydroquinoline ("FHQ"), F-4-cyclohexylpyrrolidine ("FCHP"), F-2-butyltetrahydrofuran ("FC-75"). Additional stable fluorocarbon emulsions that can achieve small particle sizes and long shelf lives when made in accordance with this invention include $(CF_3)_2CFO(CF_2CF_2)_2OCF(CF_3)_2$, $(CF_3)_2CFO(CF_2CF_2)_3OCF(CF_3)_2$, $(CF_3)_2CFO(CF_2CF_2)_2F$, $(CF_3)_2CFO(CF_2CF_2)_3F$, $(C_6F_{13})_2O$ and $F[CF(CF_3)CF_2O]_2CHFCF_3$. The present invention as it relates to the aspects of such fluorocarbon emulsion stability can be further understood by reference to the following illustrative examples.

EXAMPLE V

An emulsion of F-44E, that is $C_4F_9CH\text{-}CHC_4F_9$, was prepared by first preparing an aqueous phase. The aqueous phase was in a solution containing 2.08% weight per volume of mannitol, 18.75% weight per volume of lecithin, and 0.104 weight per volume of alpha tocopherol acetate.

The aqueous phase was buffered with 0.0515% weight per volume THAM, resulting in a pH of approximately 7.8 after the emulsion was prepared for further testing. In order to arrive at this pH, the initial pH after adding the buffer was approximately 8.2. This buffered, aqueous phase solution is sometimes designated the vehicle. The vehicle is homogenized or mixed.

The fluorocarbon F-44E was then metered in a predetermined, measured rate into the vehicle or aqueous phase to ultimately achieve 86.1% weight per volume of the F-44E in the emulsion. The resulting amounts of the emulsion components were 9% weight per volume of lecithin, 1% weight per volume of mannitol, 0.05% weight per volume of tocopherol, 0.0247% weight per volume of THAM, and 100% weight per volume of F-44E.

The resulting mixture was then placed into a flow path which was divided into a plurality of flow paths. The flows were redirected to impinge upon each other at velocities in excess of 1500 feet per second in sheets of interaction in a cavity under 4,000 pounds per square inch or more of pressure and subjected to an ice bath kept at from five degrees to eight degrees Centigrade surrounding the chamber containing the cavity. This flow procedure was repeated six times.

The emulsion was then sterilized by autoclave at 121 degrees Centigrade for eight minutes. The particle size distribution was analyzed in a Nicomp submicron particle sizer manufactured by Pacific Scientific Co. of Anaheim, Calif. This analyzer determines relative quantities of various sized particles by a method of dynamic light scattering. The fluorocarbon particles in the emulsion had a size characteristic of 188.1 nanometers mean diameter after this initial heat step.

The emulsion was then alternately frozen to minus 20 degrees Centigrade and thawed to room temperature three times. The mean fluorocarbon particle size measured after the third thaw was 193.8 nanometers. The emulsion was then subjected to three heat stress sessions of 121 degrees Centigrade for sixty minutes each. The particle size was then analyzed and found to have a characteristic mean diameter of 601.2 nanometers.

EXAMPLE VI

An emulsion of F-declin, that is C10F18, was prepared by first preparing an aqueous phase. The aqueous phase was in a solution containing 2.08% weight per volume of mannitol as an osmotic agent, 18.75% weight per volume of lecithin, and 0.104 weight per volume of alpha tocopherol acetate.

The aqueous phase was buffered with 0.0515% weight per volume THAM, resulting in a pH of approximately 7.8 after the emulsion was prepared for further testing. In order to arrive at this pH, the initial pH after adding the buffer was approximately 8.2. This buffered, aqueous phase solution is sometimes designated the vehicle. The vehicle is homogenized or mixed.

The fluorocarbon F-declin was then metered at a predetermined, measured rate into the vehicle or aqueous phase to ultimately achieve 99.53% weight per volume of the F-declin in the emulsion. The resulting amounts of the emulsion components were 9% weight per volume of lecithin, 1% weight per volume of mannitol, 0.05% weight per volume of tocopherol, 0.0247% weight per volume of THAM, and 100% weight per volume of F-declin.

The resulting mixture was then placed into a flow path which was divided into a plurality of flow paths. The flows were redirected to impinge upon each other at velocities in excess of 1500 feet per second in sheets of interaction in a cavity under 4,000 pounds per square inch or more of pressure and subjected to an ice bath as described for Example V above. This flow procedure was repeated six times.

The emulsion was then sterilized by autoclave at 121 degrees Centigrade for eight minutes. The particle size distribution was analyzed in the same Nicomp submicron particle sizer described above in Example V. The fluorocarbon particles in the emulsion had a size characteristic of 125.7 nanometers mean diameter after this initial heat step.

The emulsion was then alternately frozen to minus 20 degrees Centigrade and thawed to room temperature three times. The mean fluorocarbon particle size measured after the third thaw was 145.1 nanometers. The emulsion was then subjected to three heat stress sessions of 121 degrees Centigrade for sixty minutes each. The particle size was then analyzed and found to have a characteristic mean diameter of 86.9 nanometers.

It has been found that, in general, it is desirable to repeat the flow and impingement steps for four times, and sometimes five and six times in order to maximize stability of the emulsion. Sometimes the heat generated by the impingement has a tendency to hydrolyze lecithin. This hydrolysis can be reduced or eliminated by maintaining the cavity in which the impingement takes places in an ice bath at approximately five to ten degrees Centigrade. It should be unnecessary to cool or otherwise remove heat from the impingement cavity when an emulsifying agent which is not heat sensitive is used. Many of the fluorinated surfactants are not heat sensitive, such as triperfluoroalkylcholate and perfluoroalkylcholestanol for examples.

Fluorocarbon emulsions can be used effectively for delivery of therapeutic agents, medicines and drugs throughout the body, tissue and organs. The particles comprising the discontinuous fluorocarbon phase of the emulsion comprise two principal components, the fluorocarbon and the encasing membrane. The stability of this discontinuous fluorocarbon phase allows at least two modes of carrying the therapeutic agent, medicine or drug, namely solution of the agent, medicine or drug within the fluorocarbon phase, and complexing of the agent, medicine or drug with the membrane. Examples of medicines, drugs and therapeutic agents which dissolve in the fluorocarbon are diazepam, cyclosporin, rifampin, clindamycin, isoflurane, halothane and enflurane. Examples of medicines, therapeutic agents and drugs which do not dissolve in fluorocarbon, but which complex with, for example, a lecithin membrane include mannitol, tocopherol, streptokinase, dexamethasone, prostaglandin E, Interleukin II, gentamycin and cefoxitin. Antibiotics may be delivered transcutaneously through the skin when added to a fluorocarbon emulsion.

Thrombolytic agents, such as streptokinase and other enzymes have been transported and delivered by fluorocarbon emulsions. It is believed that the low surface tension of the fluorocarbons, and of the fluorocarbon emulsions having lecithin or fluorosurfactants as the emulsifying agent, provide a very effective wetting fluid that permeates capillaries and vascular channels, as well as other narrow channels within the body. Transport of thrombolytic agents carried by such a fluorocarbon emulsion is demonstrated by the following Example VII:

EXAMPLE VII

A 40% weight per volume perfluoroctylbromide emulsion was prepared using the method described hereinabove in Example V, having 6% weight per volume lecithin as the emulsifying agent, 0.01% weight per volume dexamethasone, 0.01% weight per volume tocopherol, 1.5% weight per volume glycerol, and having as a buffer monobasic sodium phosphate at 0.012% w/v and dibasic sodium phosphate at 0.0563% w/v. The emulsion was formulated in accordance with the procedure described hereinabove and in my co-pending application referenced herein, with the dexamethasone added during the vehicle formation. Streptokinase was added before the impingement flow steps, and three flow steps were performed.

The emulsion was placed in test tubes having clotted human blood. From 80% to 90% of the clots lysed in less than twenty minutes. Streptokinase alone, not in the presence of the fluorocarbon emulsion lyses the clots at substantially the same rate. Fluorocarbon emulsions, therefore, do not inhibit the action of the streptokinase.

The foregoing detailed description of my invention and of preferred embodiments, as to products, compositions and processes, is illustrative of specific embodiments only. It is to be understood, however, that additional embodiments may be perceived by those skilled in the art. The embodiments described herein, together with those additional embodiments, are considered to be within the scope of the present invention.

I claim:

1. A fluorocarbon emulsion, prepared by:
   combining an aqueous phase with an effective amount of emulsifying agent and a fluorocarbon to form a mixture having from greater than 50% to about 125% weight per volume of said fluorocarbon; and
   passing the fluorocarbon-containing mixture through a mechanical emulsification apparatus in which said mixture is subjected to sufficiently high flow rates and pressures to form a stable, heat sterilizable fluorocarbon-in-water emulsion;
   wherein said emulsion is biocompatible and exhibits substantial particle size stability in the non-frozen state following heat sterilization.

2. The emulsion of claim 1, wherein said emulsion further comprises an effective amount of an osmotic agent for adjusting and maintaining the osmolarity of the emulsion.

3. The emulsion of claim 1, which has been heat sterilized.

4. A storage stable, heat sterilizable fluorocarbon emulsion, comprising:
   an continuous aqueous phase, a discontinuous fluorocarbon phase, and an effective amount of emulsifying agent, wherein the concentration of said fluorocarbon phase in said emulsion is greater than 75% and no more than 125%, weight per volume, and wherein said emulsion exhibits substantial particle size stability on storage in the non-frozen state following heat sterilization and is biocompatible.

5. The emulsion of claim 4, wherein the concentration of said fluorocarbon phase in said emulsion is at least about 80%, weight per volume.

6. The emulsion of claim 4, wherein the concentration of said fluorocarbon phase in said emulsion is at least about 100%, weight per volume.

7. The fluorocarbon emulsion of claim 1 wherein the emulsifying agent is a phospholipid.

8. The fluorocarbon emulsion of claim 7 wherein the phospholipid is lecithin.

9. The fluorocarbon emulsion of claim 1 wherein the emulsifying agent is an anionic surfactant.

10. The fluorocarbon emulsion of claim 1 wherein the fluorocarbon is a mono-brominated perfluorocarbon.

11. The fluorocarbon emulsion of claim 10 wherein the mono-brominated perfluorocarbon is 1-bromoseptadecafluoroctane.

12. The fluorocarbon emulsion of claim 10 wherein the mono-brominated perfluorocarbon is 1-bromo-tridecafluorohexane.

13. The fluorocarbon emulsion of claim 10 wherein the mono-brominated perfluorocarbon is 1-bromopentadecafluoroseptane.

14. The fluorocarbon emulsion of claim 1 wherein the fluorocarbon is C4F9CH-CHC4F9.

15. The fluorocarbon emulsion of claim 1, wherein the fluorocarbon is F-decalin.

16. The fluorocarbon emulsion of claim 1 wherein the emulsifying agent comprises a biocompatible fluorinated surfactant.

17. The fluorocarbon emulsion of claim 16 wherein the fluorocarbon emulsion and fluorinated surfactant have a sufficient elimination rate that the fluorocarbon emulsion and fluorinated cosurfactant are substantially eliminated from the animal body or organ before carcinosis occurs.

18. The fluorocarbon emulsion of claim 16 wherein the fluorocarbon emulsion and fluorinated surfactant have a sufficient elimination rate that the fluorocarbon emulsion and fluorinated cosurfactant are substantially eliminated from the animal body or organ before teratogenesis occurs.

19. The fluorocarbon emulsion of claim 16 wherein the fluorocarbon emulsion and fluorinated surfactant have a sufficient elimination rate that the fluorocarbon emulsion and fluorinated cosurfactant are substantially eliminated from the animal body or organ before embryotoxicity occurs.

20. The fluorocarbon emulsion of claim 16 wherein the fluorinated cosurfactant comprises a fluorinated polyhydroxylated surfactant.

21. The fluorocarbon emulsion of claim 1 further comprising a buffering agent selected from the group consisting of imidazole, tris(hydroxymethyl)aminomethane, and combinations thereof.

22. The fluorocarbon emulsion of claim 21 wherein said buffering agent group further consists of sodium bicarbonate, monobasic sodium phosphate, dibasic sodium phosphate, magnesium sulfate, magnesium chloride, sodium chloride, potassium chloride, monobasic potassium phosphate, dibasic potassium phosphate and non-calcium precipitating combinations thereof.

23. The fluorocarbon emulsion of claim 21 wherein the pH of the emulsion is maintained at from approximately 4.0 to approximately 8.4 after sterilization and before use intravenously.

24. The fluorocarbon emulsion of claim 21 for use wherein the pH of the emulsion is maintained at from approximately 7.0 to approximately 7.8 before use in the coronary arteries.

25. The fluorocarbon emulsion of claim 21 wherein said buffering agent is imidazole.

26. The fluorocarbon emulsion of claim 1 further comprising an anti-oxidant.

27. The fluorocarbon emulsion of claim 26 wherein said anti-oxidant comprises mannitol.

28. The fluorocarbon emulsion of claim 26 wherein the anti-oxidant comprises a tocopherol.

29. The fluorocarbon emulsion of claim 26 wherein the anti-oxidant comprises mannitol and tocopherol.

30. The fluorocarbon emulsion of claim 28 wherein the tocopherol comprises alpha-tocopherol acetate.

31. The fluorocarbon emulsion of claim 26 including an anti-oxidant for reduction of oxidation of components of said emulsion comprising an effective amount of an anti-oxidant selected from the group consisting of ascorbyl palmitate, mannitol, tocopherol, imidazole and combinations thereof.

32. The fluorocarbon emulsion of claim 26 including an anti-oxidant for reduction of oxidation of tissues of animal bodies and organs thereof comprising an effective amount of an anti-oxidant selected from the group consisting of ascorbyl palmitate, mannitol, tocopherol, imidazole and combinations thereof.

33. The fluorocarbon emulsion of claim 1 for application to tissue of animal bodies and organs thereof, further comprising mannitol and tocopherol in an effective amount for reduction of oxidation in said emulsion.

34. The fluorocarbon emulsion of claim 1 for application to tissue of animal bodies and organs thereof, further comprising mannitol and tocopherolan in an effective amount for reduction of oxidation in said tissue of animal bodies and organs thereof.

35. The fluorocarbon emulsion of claim 1 for application to tissue of animal bodies and organs thereof, further comprising mannitol in an effective amount for reduction of oxidation in said emulsion.

36. The fluorocarbon emulsion of claim 1 for application to tissue of animal bodies and organs thereof, further comprising mannitol in an effective amount for reduction of oxidation in said tissue of animal bodies and organs thereof.

37. The fluorocarbon emulsion of claim 31 for application to tissue of animal bodies and organs thereof for reduction of oxidation therein wherein said anti-oxidant group further includes ascorbic acid, salts and complexes thereof and non-calcium precipitating combinations thereof.

38. The fluorocarbon emulsion of claim 1 wherein the fluorocarbon in emulsion is in an amount of from 80% weight per volume to 125% weight per volume.

39. The fluorocarbon emulsion of claim 2, wherein the osmolarity of the emulsion is maintained between from about 240 milliosmols to about 650 milliosmoles.

40. The fluorocarbon emulsion of claim 2, wherein the osmolarity of the emulsion is maintained between from about 300 milliosmols to about 450 milliosmols.

41. The fluorocarbon emulsion of claim 39 or 40, wherein the osmolarity is maintained, at least in part, by a hexahydric alcohol.

42. The fluorocarbon emulsion of claim 41, wherein the hexahydric alcohol is selected from the group consisting of mannitol and sorbitol.

43. The fluorocarbon emulsion of claim 42, wherein the hexahydric alcohol is mannitol, present at a concentration of from about 0.25% weight per volume to about 1.5% weight per volume.

44. The fluorocarbon emulsion of claim 39 or 40, wherein the osmolarity is maintained, at least in part, by a sugar.

45. The fluorocarbon emulsions of claim 44, wherein the sugar is selected from the group consisting of glucose, mannose and fructose, or combinations thereof.

46. The fluorocarbon emulsion of claim 39 or 40, wherein the osmolarity is maintained, at least in part, by a buffering agent.

47. The fluorocarbon emulsion of claim 39 or 40, wherein the osmolarity is maintained, at least in part, by chloride or sulfate salts.

* * * * *